United States Patent
Maragni et al.

(10) Patent No.: US 8,183,391 B2
(45) Date of Patent: May 22, 2012

(54) PROCESS FOR PREPARING DORZOLAMIDE

(75) Inventors: Paolo Maragni, Virgilio (IT); Ivan Michieletto, Venice (IT); Livius Cotarca, Cervignano del Friuli (IT)

(73) Assignee: Zach Systems S.p.A., Milan (IT)

( * ) Notice: Subject to any disclaimer, the term of this patent is extended or adjusted under 35 U.S.C. 154(b) by 827 days.

(21) Appl. No.: 12/296,834

(22) PCT Filed: Apr. 16, 2007

(86) PCT No.: PCT/EP2007/053691
§ 371 (c)(1),
(2), (4) Date: Oct. 10, 2008

(87) PCT Pub. No.: WO2007/122130
PCT Pub. Date: Nov. 1, 2007

(65) Prior Publication Data
US 2009/0275759 A1    Nov. 5, 2009

(30) Foreign Application Priority Data
Apr. 21, 2006  (EP) .................................. 06112883

(51) Int. Cl.
*C07D 333/34* (2006.01)
*A61K 31/38* (2006.01)

(52) U.S. Cl. .............. 549/66; 549/23; 549/28; 514/432; 514/444

(58) Field of Classification Search ....................... None
See application file for complete search history.

(56) References Cited

U.S. PATENT DOCUMENTS

| | | | | |
|---|---|---|---|---|
| 3,810,899 A | * | 5/1974 | Mohaesi et al. ............... | 546/74 |
| 4,497,813 A | * | 2/1985 | Ostermayer et al. .......... | 514/166 |
| 2005/0059696 A1 | | 3/2005 | Reddy et al. | |
| 2005/0131073 A1 | | 6/2005 | Schlummer et al. | |

FOREIGN PATENT DOCUMENTS

EP    0296879 A1    12/1988

OTHER PUBLICATIONS

International Search Report and Written Opinion of the International Searching Authority issued for the corresponding PCT International Application No. PCT/EP2007/053691, Jun. 20, 2007.

* cited by examiner

*Primary Examiner* — Yate K Cutliff
(74) *Attorney, Agent, or Firm* — Lucas & Mercanti, LLP

(57) ABSTRACT

A process for resolving dorzolamide trans racemate, which comprises reacting said racemate with (1S)-(+)-10-camphorsulfonic acid so obtaining the (4S,6S) enantiomer by selectively precipitating and recovering the camphorsulfonic acid salt thereof (dorzolamide camphorsulfonate), and neutralizing dorzolamide camphorsulfonate to obtain dorzolamide.

7 Claims, No Drawings

PROCESS FOR PREPARING DORZOLAMIDE

CROSS REFERENCE TO RELATED APPLICATIONS

This application is the United States national phase filing of the corresponding international application number PCT/EP2007/053691, filed on Apr. 16, 2007, which claims priority to and benefit of European application no. 06112883.1, filed Apr. 21, 2006, which applications are hereby incorporated by reference in their entirety.

The present invention relates to a process for preparing (4S,6S)-4-(Ethylamino)-5,6-dihydro-6-methyl-4H-thieno[2,3-b]thiopyran-2-sulfonamide 7,7-dioxide (hereinafter also referred to as dorzolamide) of formula (I)

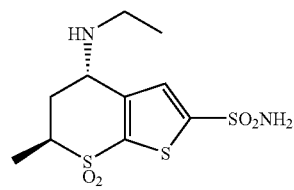
(I)

Dorzolamide monohydrochloride is a commercially marketed pharmaceutical substance, useful for the treatment of elevated intraocular pressure in patients with ocular hypertension or open-angle glaucoma.

Dorzolamide hydrochloride was first disclosed in the European patent EP 296879. According to this patent, dorzolamide can be prepared following a multi-step process, which comprises the chromatographic separation of the racemic trans-diastereomer (4S,6S; 4R,6R) 4-(Ethylamino)-5,6-dihydro-6-methyl-4H-thieno[2,3-b]thiopyran-2-sulfonamide 7,7-dioxide (dorzolamide trans racemate) from the unwanted racemic cis-diastereomer (dorzolamide cis racemate), the resolution of dorzolamide trans racemate by forming diastereomeric salts with the optically active (−) di-p-toluoyl-L-tartaric acid, the isolation of the dorzolamide di-p-toluoyl-L-tartrate salt (dorzolamide tartrate), the subsequent purification phase of the salt through recrystallizations, the liberation of dorzolamide with aqueous NaHCO$_3$ and the final extraction of dorzolamide with ethyl acetate.

It is well known that the resolution of racemic mixtures via diastereomeric salt formation is one of the most commonly used industrial technique. It is also known that besides tartaric acid and its derivatives such as, e.g., di-toluoyl-tartaric acid, other optically active acids, such as malic acids, mandelic acid and its derivatives, α-methoxyphenylacetic acid, α-methoxy-α-trifluoromethyl-phenylacetic acid, 1-camphor-10-sulphonic acid and its derivatives, can be alternatively used to resolve racemic compounds containing an amine group in their structure. A person skilled in the art could have therefore selected one of the resolution agents listed above, in the expectation of obtaining results similar than the results obtained with di-p-toluoyl-L-tartaric acid.

It has now unexpectedly found that the use of (1S)-(+)-10camphorsulphonic acid in place of di-p-toluoyl-L-tartaric acid as resolving agent of the dorzolamide trans racemate, not only allows to obtain better results in terms of enantiomeric purity of the corresponding salt, but also it allows to considerably reduce the amount of the undesired diastomer dorzolamide cis racemate, which is present as impurity in the dorzolamide trans racemate.

It is therefore a first object of the present invention a process for resolving trans racemic (±) (4S,6S;4R,6R)-4-(Ethylamino)-5,6-dihydro-6-methyl-4H-thieno-[2,3-b]thiopyran-2-sulfon-amide 7,7-dioxide (dorzolamide trans racemate), of formula (II)

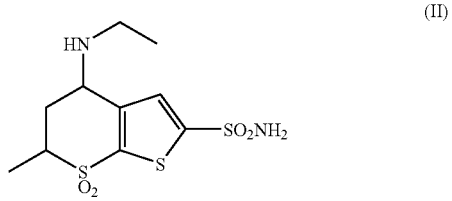
(II)

characterized by:
a) reacting said racemate with (1S)-(+)-10-camphorsulfonic acid of formula

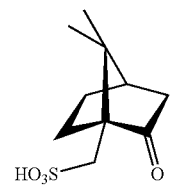

b) obtaining the (4S,6S) enantiomer by selectively precipitating and recovering the camphorsulfonic acid salt thereof (dorzolamide camphorsulfonate) of formula (III)

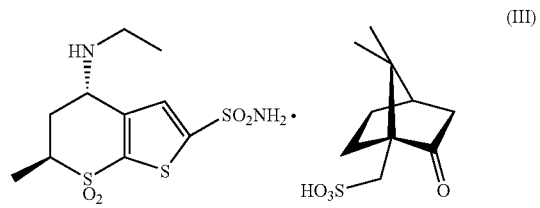
(III)

and
c) neutralizing dorzolamide camphorsulfonate of formula (III) to obtain the compound of formula (I).

The resolving agent (1S)-(+)-10-camphorsulfonic acid is commercially available or can be prepared by methods well known in the art.

The resolution step can be carried out reacting dorzolamide trans racemate with (1S)-(+)-10-camphorsulfonic acid, in a solvent capable of dissolving both of the foregoing reagents and of selectively precipitating the camphorsulfonic acid salt of the corresponding (4S,6S) enantiomer (dorzolamide camphorsulfonate). Examples of suitable solvents include lower alcohols such as methanol, ethanol and 2-propanol, and mixture of one of these alcohols with water. Preferred solvents are 2-propanol and 2-propanol/water mixtures.

The reaction temperature can range from about room temperature to about 82° C. Dorzolamide camphorsulfonate can then be collected in a solid state as a crystalline substance using conventional techniques such as, for example, vacuum filtration.

If desired, dorzolamide camphorsulfonate can be submitted to a further purification, in order to promote the enantiomeric enrichment of the enantiomer achieved and to improve its overall purity profile. In an example, dorzolamide camphorsulfonate can be recrystallized from suitable organic solvents including alcoholic solvents such as methanol, ethanol, 2-propanol and mixture of these alcohols with water. Preferred solvents are 2-propanol and 2-propanol/water mixtures.

Dorzolamide camphorsulfonate is neutralized, to recover the free base of the (4S,6S) enantiomer, i.e. dorzolamide. Such neutralization can be accomplished by reacting the salt with an appropriate alkaline agent, using methods well known to those skilled in the art. For example, dorzolamide camphorsulfonate can be treated with an aqueous base such as sodium or potassium hydroxide or potassium carbonate. Dorzolamide can be directly obtained through the extraction of the alkaline medium containing dorzolamide with suitable organic solvents non-miscible in water, such as, for example, ethyl-acetate.

If desired, dorzolamide can be further transformed into the corresponding hydrochloride salt following conventional techniques, for example following the procedure described in EP 296879.

Dorzolamide trans racemate of formula (II) can be obtained from the crude diastereomeric mixture of dorzolamide trans- and cis-racemates by chromatography separation according to procedures well known in the art or by selective crystallization. Separation through selective crystallization can be performed, for example, by reacting the crude diastereomeric mixture of dorzolamide trans and cis racemates with maleic acid of formula

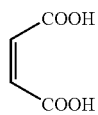

so obtaining the trans racemate by isolating dorzolamide trans racemate maleate salt of formula (IV)

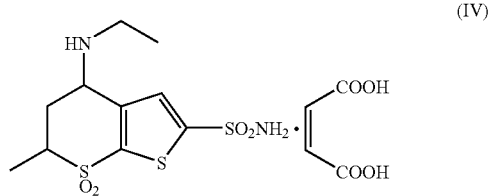

(IV)

and neutralizing said salt of formula (IV) to obtain dorzolamide trans racemate of formula (II).

The separation step can be carried out by mixing the crude diastereomeric mixture of the foregoing dorzolamide trans and cis racemates with maleic acid in a suitable organic solvent such as, for example, acetone or a mixture acetone/ethyl acetate. Acetone is preferred. The maleate salt can be then isolated by filtration.

The preparation of the crude diastereomeric mixture of the foregoing dorzolamide trans and cis-racemates can be carried out, for example, following the procedure described in EP 296879.

Maleic acid is commercially available or can be prepared by methods well known in the art.

A further aspect of the invention relates to the camphorsulfonic acid salt of (4S,6S) 4-(Ethylamino)-5,6-dihydro-6-methyl-4H-thieno[2,3-b]thiopyran -2-sulfonamide-7,7-dioxide (dorzolamide camphorsulfonate) of formula (III) and its use in the preparation of dorzolamide monohydrochloride.

According to the present invention, the (R) and (S) denotation indicates the stereo configuration, and (+) and (−) denotation indicates the optical activity of the compounds of the present invention.

The following examples illustrates but do not limit the present invention.

EXAMPLES

Example 1

Preparation of (±)-trans-(4S,6S;4R,6R)-4-(Ethylamino)-5,6-dihydro-6-methyl-4H-thieno[2,3-b]thiopyran-2-sulfonamide 7,7-dioxide, maleate of formula (IV) (Dorzolamide trans racemate, maleate salt).

Crude racemic 4-(Ethylamino)-5,6-dihydro-6-methyl-4H-thieno[2,3-b]thiopyran-2-sulfonamide-7, 7-dioxide (18.9 g; corresponding to 34.37 mmol of a 80/20 trans/cis diastereomers mixture) was dissolved in acetone (70 mL) at 50° C. A solution of maleic acid (4.03 g) in acetone (18 mL) was then added over about 20 minutes. The so obtained suspension was stirred at 50° C. over 1 hour and then cooled to 20° C. over 3 hours. The resulting solid was isolated by vacuum filtration washing with acetone (20 mL) and then dried in vacuum oven at 50° C. to give the title compound (12.4 g; trans/cis ratio ≧ 95/5) as a white solid.

Example 2

Preparation of (4S,6S)-4-(Ethylamino)-5,6-dihydro-6-methyl-4H-thieno[2,3-b]thio-pyran-2-sulfonamide-7,7-dioxide,(1S)-(+)-10-camphorsulfonate of formula (III) (Dorzolamide camphorsulfonate).

Dorzolamide trans racemate of formula (II) (9.2 g) and (1S)-(+)-10-camphorsulfonic acid (2.9 g) were dissolved in a mixture of 2-propanol/water (about 88/12 w/w) (711 g). The so obtained solution was distilled at normal pressure up to a final volume of 550 mL and cooled to 20° C. The resulting suspension was stirred at 20° C. over 7 hours. The solid was isolated by vacuum filtration washing with 2-propanol (2×10 mL) and then dried in vacuum oven at 50° C. to give Dorzolamide camphorsulfonate ($1^{st}$ crop) (5 g). This compound (5 g) was dissolved in a mixture of 2-propanol (247 g) and water (75 g) by heating at reflux. The so obtained solution was distilled at normal pressure collecting about 225 g of azeotropic mixture 2-propanol/water. An additional amount of 2-propanol (210 g) was charged into the reactor and the solution was distilled at normal pressure up to a final volume of 110-120 mL. The resulting suspension was stirred at reflux for additional 2 hours and then cooled to 20° C. over 7 hours. The resulting solid was isolated by vacuum filtration washing with 2-propanol (2×20 mL) and then dried in vacuum oven at 50° C. to give the title compound (4.9 g; >99% e.e.) as a white solid.

Example 3

Preparation of (4S,6S)-4-(Ethylamino)-5,6-dihydro-6-methyl-4H-thieno[2,3-b]thio-pyran-2-sulfonamide-7,7-dioxide, (−)-di-p-toluoyl-L-tartrate (Dorzolamide tartrate).

Dorzolamide trans racemate of formula (II) (0.8 g) and (−)-di-p-toluoyl-L-tartaric acid (0.22 g) were dissolved in refluxing 2-propanol (45 mL). The so obtained solution was distilled at normal pressure up to a final volume of 20 mL. The resulting suspension was stirred at refluxing temperature further 2 hours and then cooled to 20° C. over 7 hours. The solid was isolated by vacuum filtration washing with 2-propanol (4 mL) and then dried in vacuum oven at 40° C. to give Dorzolamide tartrate (1$^{st}$ crop) (0.626 g). This compound (0.601 g) was dissolved in refluxing 2-propanol and the solution was distilled at normal pressure up to a final volume of 18 mL. The resulting suspension was cooled to 20° C. over 7 hours. The solid was isolated by vacuum filtration washing with 2-propanol (4 mL) and then dried in vacuum oven at 40° C. to give Dorzolamide tartrate (2$^{nd}$ crop) (0.49 g). This compound was submitted to a further re-crystallization following the latter procedure (the solution was distilled at normal pressure up to a final volume of 15 mL). The resulting solid was isolated by vacuum filtration then dried in vacuum oven at 50° C. to give the title compound (0.379 g; 85-87% e.e.) as a white solid.

Example 4

An experimental test has been carried out to compare enantiomeric purity measured as enantiomeric excess (% e.e.) of dorzolamide tartrate and dorzolamide camphorsulfonate obtained by reacting dorzolamide trans racemate with (−) di-p-toluoyl-L -tartaric acid and (1S)-(+)-10-camphorsulfonic acid respectively.

All the crystallization experiment have been carried out using 2-propanol or a mixture of 2-propanol/water as the solvent, following the procedure outlined in Example 2 and Example 3. The obtained results are reporte in the Table 1 below.

TABLE 1

| Compound | % e.e. (*) |
|---|---|
| Dorzolamide trans racemate | 0 |
| Dorzolamide tartrate | 56.7 (1$^{st}$ crystallization) |
| | 72.2 (2$^{nd}$ crystallization) |
| | 85.7-87.4 (3$^{rd}$ crystallization) |
| Dorzolamide camphorsulphonate | 99.2 (1$^{st}$ crystallization) |
| | >99.9 (2$^{nd}$ crystallization) |

(*): $\% \text{ e.e.} = \frac{(A_{S,S} - A_{R,R})}{(A_{S,S} + A_{R,R})} * 100$ (A = Area determinated by HPLC analysis)

The above tabulated data clearly show the surprising superior enantiomeric purity achieved when (1S)-(+)-10-camphorsulfonic acid is used instead of (−) di-p -toluoyl-L-tartaric acid as resolving agent.

Example 5

An experimental test has been carried out to determine the amount of cis-diastereomer, expressed as % ratio of HPLC Areas, still present as residual impurity in dorzolamide trans racemate, dorzolamide tartrate and dorzolamide camphorsulfonate obtained by reacting dorzolamide trans racemate with (−)-di-p-toluoyl-L -tartaric acid and (1S)-(+)-10-camphorsulfonic acid respectively.

All the crystallization experiment have been carried out using 2-propanol or a mixture of 2-propanol/water as the solvent, following the procedure outlined in Example 2 and Example 3. The obtained results are reported in the Table 2 below.

TABLE 2

| Compound | % cis-diastereomer impurity (**) |
|---|---|
| Dorzolamide trans racemate | 4.6-4.9 |
| Dorzolamide tartrate | 4.3 (1$^{st}$ crystallization) |
| | n.a. (2$^{nd}$ crystallization) |
| | 3.0 (3$^{rd}$ crystallization) |
| Dorzolamide camphorsulphonate | 1.03 (1$^{st}$ crystallization) |
| | 0.26 (2$^{nd}$ crystallization) |

(**): $\% \text{ cis} = \frac{A_{Cis}}{(A_{Cis} + A_{Trans})} * 100$ (A = Area determinated by HPLC)

The above tabulated data clearly show the unexpected decrease of the presence of cis impurity achieved when (1S)-(+)-10-camphorsulfonic acid is used instead of (−) di-p-toluoyl-L-tartaric acid as resolving agent.

The invention claimed is:

1. A process for resolving trans racemic (±) (4S,6S, 4R,6R)-4-(Ethylamino)-5,6-dihydro-6-methyl-4H-thieno[2,3-b]thiopyran-2-sulfonamide 7,7-dioxide (dorzolamide trans racemate), of formula (II)

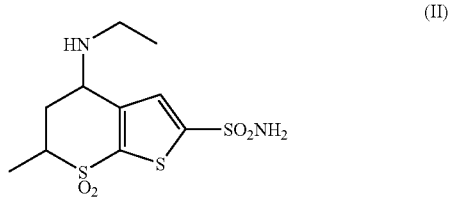

comprising a) reacting said racemate with (1S)-(+)-10-camphorsulfonic acid of formula

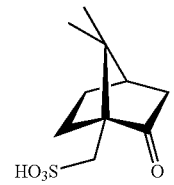

b) obtaining the (4S, 6S) enantiomer by selectively precipitating and isolating (4S,6S) camphorsulfonic acid salt (dorzolamide camphorsulfonate) of formula (III)

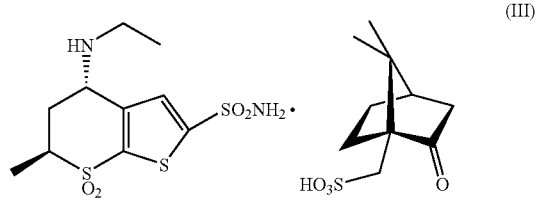

and c) neutralizing dorzolamide camphorsulfonate of formula (III) to obtain dorzolamide of formula (I)

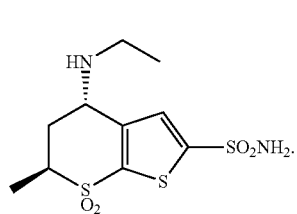

(I)

2. The process according to claim 1, wherein the reaction of the racemate with the camphorsulfonic acid is carried out in a solvent capable of dissolving said process reactants comprising the racemate and the camphorsulfonic acid, and of selectively precipitating the camphorsulfonic acid salt of the corresponding (4S,6S) enantiomer (dorzolamide camphorsulfonate).

3. The process according to claim 2, wherein said solvent is a 2-propanol/water mixture.

4. The process according to claim 1, wherein after said isolation by precipitation, dorzolamide camphorsulfonate is submitted to a further purification through recrystallization to promote enantiomeric enrichment of the (4S,6S) enantiomer achieved and to improve its overall purity profile.

5. The process according to claim 1, wherein dorzolamide trans racemate is obtained by reacting a diastereomeric mixture of dorzolamide trans and cis racemates with maleic acid of formula

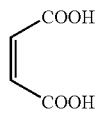

so obtaining trans racemate by isolating dorzolamide trans racemate maleate salt of formula (IV)

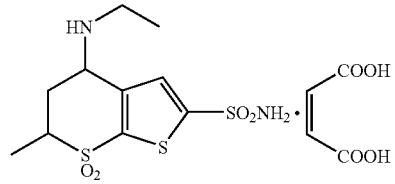

(IV)

and neutralizing said salt.

6. A camphorsulfonic acid salt of (4S,6S) 4-(Ethylamino)-5,6-dihydro-6-methyl-4H-thieno[2,3-b]thiopyran-2-sulfonamide-7,7 dioxide (dorzolamide camphorsulfonate) of formula (III).

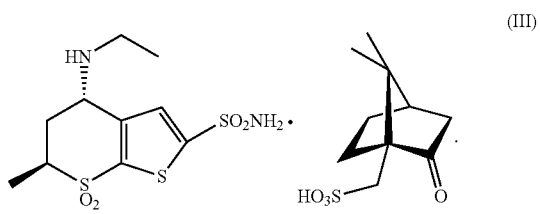

(III)

7. The process according to claim 3 for manufacturing dorzolamide with a compound of formula (III).

* * * * *